US006896926B2

(12) United States Patent
Qiu et al.

(10) Patent No.: US 6,896,926 B2
(45) Date of Patent: May 24, 2005

(54) METHOD FOR APPLYING AN LBL COATING ONTO A MEDICAL DEVICE

(75) Inventors: Yongxing Qiu, Duluth, GA (US); Lynn Cook Winterton, Alpharetta, GA (US); John Martin Lally, Lilburn, GA (US); Yasuo Matsuzawa, Roswell, GA (US)

(73) Assignee: Novartis AG, Basel (CH)

( * ) Notice: Subject to any disclaimer, the term of this patent is extended or adjusted under 35 U.S.C. 154(b) by 71 days.

(21) Appl. No.: 10/654,340

(22) Filed: Sep. 3, 2003

(65) Prior Publication Data

US 2004/0047979 A1 Mar. 11, 2004

Related U.S. Application Data

(60) Provisional application No. 60/409,945, filed on Sep. 11, 2002.

(51) Int. Cl.$^7$ ............................. A61L 27/00; B05D 1/36; B05D 1/38
(52) U.S. Cl. ........................ 427/2.31; 427/2.1; 427/2.24; 427/402; 427/407.1; 427/414; 427/415; 427/421; 427/430.1
(58) Field of Search .................... 427/2.1, 2.24, 427/2.31, 402, 407.1, 414–415, 421, 430.1

(56) References Cited

U.S. PATENT DOCUMENTS

| | | | | |
|---|---|---|---|---|
| 4,168,112 A | | 9/1979 | Ellis et al. .................. 351/160 |
| 4,321,261 A | | 3/1982 | Ellis et al. .................. 424/180 |
| 4,941,997 A | | 7/1990 | Decher et al. ............... 252/586 |
| 4,973,429 A | | 11/1990 | Decher et al. ............... 252/587 |
| 5,068,318 A | | 11/1991 | Decher et al. ............... 534/573 |
| 5,208,111 A | | 5/1993 | Decher et al. ............... 428/420 |
| 5,518,767 A | | 5/1996 | Rubner et al. ............... 427/259 |
| 5,529,727 A | | 6/1996 | LaBombard et al. ........ 264/1.36 |
| 5,536,573 A | | 7/1996 | Rubner et al. ............... 428/378 |
| 5,700,559 A | * | 12/1997 | Sheu et al. ............... 428/319.7 |
| 6,011,082 A | | 1/2000 | Wang et al. ................. 523/107 |
| 6,451,871 B1 | | 9/2002 | Winterton et al. .......... 523/106 |
| 2001/0045676 A1 | | 11/2001 | Winterton et al. ........... 264/2.5 |
| 2001/0048975 A1 | | 12/2001 | Winterton et al. ........ 427/412.1 |
| 2002/0006493 A1 | | 1/2002 | Chabrecek et al. ......... 428/64.1 |
| 2002/0086160 A1 | | 7/2002 | Qiu et al. .................... 428/413 |
| 2002/0182316 A1 | | 12/2002 | Gilliard et al ............... 427/162 |
| 2003/0008154 A1 | | 1/2003 | Aguado et al. ............. 428/447 |
| 2003/0012872 A1 | | 1/2003 | Qiu et al. .................... 427/162 |
| 2003/0039742 A1 | | 2/2003 | Qiu et al. ..................... 427/2.1 |
| 2003/0117579 A1 | | 6/2003 | Morris et al. ................ 351/200 |
| 2003/0134132 A1 | | 7/2003 | Winterton et al. ........... 428/451 |

FOREIGN PATENT DOCUMENTS

| | | |
|---|---|---|
| EP | 0 032 443 | 5/1985 |
| EP | 0 138 385 | 4/1990 |
| GB | 2 102 070 | 1/1983 |
| JP | 1-158412 | * 6/1989 |
| JP | 5-318118 | * 12/1993 |
| WO | WO 95/00618 | 1/1995 |
| WO | WO 95/02251 | 1/1995 |
| WO | WO 95/20407 | 8/1995 |
| WO | WO 96/18498 | 6/1996 |
| WO | WO 96/31792 | 10/1996 |
| WO | WO 96/37241 | 11/1996 |
| WO | WO 99/35520 | * 7/1999 ............ G02B/1/04 |
| WO | WO 01/57118 | 8/2001 |
| WO | WO 01/92924 | 12/2001 |
| WO | WO 02/16974 | 2/2002 |
| WO | WO 02/097481 | 12/2002 |

OTHER PUBLICATIONS

European Search Report.

Decher, Lehr, Lowack, Lvov & Schmitt, "New Nanocomposite Films for Biosensors: layer by Layer adsorbed films of polyelectrolytes, proteins or DNA", 1994, pp677–684.

Sukhorukov, Mohwald, Decher and Lvov, "Assembly of Polyelectrolyte Multilayer films by consecutively alternating adsorption of Polynucleotides and Polycations", 1996, pp. 220–223.

Uchida, Kunitake, and Kajiyama, "Blood Compatibility—Surface Characteristic Relationships of a Langmuir–Blodgett Film COmposed of an Anionic Amphiphile–Polycation COmplex", 1994, pp. 199–211.

Onitsuka, Fou, Ferreira, Hsieh, and Rubner, "Enhancement of Light Emitting Diodes Based on Self–Assembled Heterostructures of Poly(p–PHenylene Vinylene)", 1996, pp. 4067–4071.

Yoo, Lee and Rybner, "Investigations of New Self–Assembled Multilayer Thin Films Based on Alternately Adsorbed Layers of Polyelectrolytes and Functional Dye Molecules", 1996, pp. 395–400.

Yoo, Wu, Lee and Rubner, "New Electro–Active Self–Assembled MultiLayer Thin Films Based on Alternately Adsorbed Layers of Polyelectrolytes and Functional Dye Molecules", 1997, pp. 1425–1426.

Yoo & rubner, "Layer–By–Layer Modification of Surfaces Through The USe of Self Assembled Monolayers of Polyions", 1995, pp. 2568–174.

Ferreira and Rubner, "Molecular Level Processing of Conjugated Polymers. Layer by Layer Manipulation of Conjugated Polyions", 1995, pp. 7107–7114.

(Continued)

*Primary Examiner*—Jennifer Kolb Michener
(74) *Attorney, Agent, or Firm*—Jian Zhou; Robert Gorman; R. Scott Meece

(57) ABSTRACT

The present invention provides an improved LbL-coating process for modifying the surface of a medical device, preferably an ophthalmic device, more preferably a contact lens. An LbL coating on a contact lens, which is prepared according to the process of the invention, can have increased hydrophilicity characterized by an averaged contact angle of about 80 degree or less, preferably about 50 degrees or less, while maintaining the desired bulk properties such as oxygen permeability and ion permeability of lens material.

13 Claims, No Drawings

OTHER PUBLICATIONS

Fou and Rubner, "Molecular Level Processing of Conjugated Polymers. Layer by Layer Manipulation of In–Situ Polymerized p–Type Doped Conducting Polymers", 1995, pp. 7115–7120.

Cheung, Stockton & Rubner, "Molecular Level Processing of Conjugated Polymers. Layer by Layer Manipulation of Polyanilene via Electrostatic Interactions", 1995, pp. 2712–2716.

Cheung, Fou, Ferreira and Rubner, "Molecular Self Assembly of Conducting Polymers: A New Layer by Layer Thin Film Deposition Process", pp. 757–758.

Vargo, Clavert, Wynne, Avlyanov, MacDiamid, and Rubner, "Patterned Polymer multilayer Fabrication by Controlled Adhesion of Polyelectrolytes to Plasma modified Fluoropolymer Surfaces", 1996, pp. 169–174.

Winterton, Qiu, and Lally, "Coating for Biomedical Devices", 2002, pp. 1–2.

International Search Report.

* cited by examiner

METHOD FOR APPLYING AN LBL COATING ONTO A MEDICAL DEVICE

This application claims the benefit under USC §119 (e) of U.S. provisional application No. 60/409,945 filed Sep. 11, 2002, incorporated by reference in its entirety.

The present invention generally relates to a method for applying an LbL coating onto a medical device, preferably an ophthalmic device, more preferably a contact lens, to improve the hydrophilicity and lubricity of the medical device.

BACKGROUND OF THE INVENTION

Many devices used in biomedical applications require that the bulk of the device has one property and the surfaces of the device have a different property. For example, contact lenses may require relatively high oxygen permeability through the bulk of the lens to maintain good corneal health. However, materials that exhibit exceptionally high oxygen permeability (e.g. polysiloxanes) are typically hydrophobic and, will up take lipid or protein from the ocular environment and may adhere to the eye if not treated or surface-modified. Thus, a contact lens will generally have a core or bulk material that is highly oxygen permeable and hydrophobic, and a surface that has been treated or coated to increase hydrophilic properties. This hydrophilic surface allows the lens to move relatively freely on the eye without absorbing excessive amounts of tear lipid and protein.

In order to modify the hydrophilic nature of a relatively hydrophobic contact lens material, a coating may be applied onto the surface of a contact lens using a number of technologies, including a plasma treatment process (e.g., PCT Publication Nos. WO 96/31793, WO 99/57581, WO 94/06485), a Langmuir-Blodgett deposition process (e.g., U.S. Pat. Nos. 4,941,997; 4,973,429; and 5,068,318), a controlled spin casting process, a chemisorption process, a vapor deposition or a layer-by-layer polymer adsorption process that is preceded by a charge inducing process. These techniques are not cost-effective and are difficult to be implemented in an automated production process.

Another coating technique is a layer-by-layer ("LbL") polyelectrolyte absorption process. For example, Yoo, et al. reported a process which involves alternatively dipping hydrophilic glass substrates in a polyelectrolyte solution (e.g., polycations such as polyallylamine or polyethyleneimine) and then in an oppositely charged solution to form electrically conducting thin films and light-emitting diodides (LEDs) (Yoo, et al., "Investigation of New Self-Assembled Multilayer Thin Films Based on Alternately Adsorbed Layers of Polyelectrolytes and Functional Dye Molecules", Mat. Res. Soc. Symp. Proc. 413: 395–400 (1996)).

A series of three articles described similar LbL polyelectrolyte absorption processes (Ferreira & Rubner, Macromolecules, 28: 7107–7114 (1995); Fou & Rubner, Macromolecules, 28: 7115–7120 (1995); and Cheung et al., Macromolecules, 30:2712–2716 (1997)). These processes involve treating glass substrates that have hydrophilic, hydrophobic, negatively, or positively charged surfaces. The glass surfaces are treated for extended periods in hot acid baths and peroxide/ammonia baths to produce a hydrophilic surface. Hydrophobic surfaces are produced by gas-phase treatment in the presence of 1,1,1,3,3,3-hexamethyldisilazine for 36 hours. Charged surfaces are prepared by covalently anchoring charges onto the surface of the hydrophilic slides. For example, positively charged surfaces are made by further treating the hydrophilic surfaces in methanol, methanol/toluene, and pure toluene rinses, followed by immersion in (N-2 aminoethyl-3-aminopropyl) trimethyloxysilane solution for 12 to 15 hours. This procedure produces glass slides with amine functionalities, which are positively charged at a low pH.

U.S. Pat. Nos. 5,518,767 and 5,536,573 to Rubner et al. describe methods of producing bilayers of p-type doped electrically conductive polycationic polymers and polyanions or water-soluble, non-ionic polymers on glass substrates. These patents describe extensive chemical pre-treatments of glass substrates that are similar to those described in the aforementioned articles.

U.S. Pat. No. 5,208,111 to Decher et al. describes a method for applying one or more layers to a support modified by the applications of ions and ionizable compounds of the same charges over the entire area. The one or more layers are made of organic materials which in each layer contain ions of the same charge, the ions of the first layer having the opposite charge of the modified support and in the case of several layers each further layer having again the opposite charge of the previous layer.

U.S. Pat. No. 5,700,559 to Sheu et al. discloses a method for making a hydrophilic article having a substrate, an ionic polymeric layer bonded directly onto the substrate, and a disordered polyelectrolyte coating ionically bonded to the ionic polymeric layer. The ionic polymeric layer is obtained by a plasma treatment, an electron beam treatment, a corona discharge, an X-ray treatment, or an acid/base chemical modification of the substrate.

Although each of these surface modification techniques are effective for producing an article with a surface that is different from the remainder of the article, the modification processes requires complex and time-consuming pretreatment of the substrate surface to obtain a highly charged surface.

To overcome this problem, various layer-by-layer (LbL) polyelectrolyte deposition techniques have been developed by the assignee of the present invention (e.g., PCT Publication Nos. WO 01/57118, WO 99/35520). For example, one LbL coating technique involves dipping iteratively one or more lenses in an alternating fashion to a polyanion (e.g., polyacrylic acid, PAA) solution and then a polycation (e.g., polyallylamine hydrochloride, PAH) solution, a LbL coating can be formed on the surfaces of lenses. Nevertheless, although these layer-by-layer techniques effectively alter the surfaces of various biomaterials, such as contact lenses, a need for further improvement still remains. For example, by using these LbL-coating techniques, it may not be possible to form an LbL coating which can impart desired surface properties such as high hydrophilicity and lubricity. High hydrophilicity and lubricity of an LbL coating on a contact lens may enhance wearer's comfort and/or ocular health.

SUMMARY OF THE INVENTION

The invention provides a method of applying an LbL coating onto a medical device, preferably an ophthalmic device, more preferably a contact lens, the method of invention comprising:

(a) contacting said medical device with a first coating solution containing a first polyionic material to non-covalently apply an innermost layer of the first polyionic material onto said medical device, wherein the concentration of the first polyionic material in the first coating solution is sufficiently high enough to increase the hydrophilicity of the LbL coating, and wherein said medical device is not subjected to a surface modification;

(b) contacting said medical device having the innermost layer of the first polyionic material with a second coating solution containing a second polyionic material, to form a first polyelectrolyte bilayer consisting of the innermost layer of the first polyionic material and one layer of the second polyionic material on top of the innermost layer, wherein the second polyionic material has charges opposite of the charges of the first polyionic material;

(c) contacting said medical device having the first polyelectrolyte bilayer with a third coating solution containing the first polyionic material or a third polyionic material, to form a layer of the first polyionic material or the third polyionic material on top of the first polyelectrolyte bilayer, wherein the third polyionic material has charges opposite of the charges of the second polyionic material;

(d) contacting said medical device having the first polyelectrolyte bilayer and one layer of the first polyionic material or the third polyionic material on top of the first polyelectrolyte bilayer with a fourth coating solution containing the second polyionic material or a fourth polyionic material having charges opposite of the charges of the first or third polyionic material, to form a second polyelectrolyte bilayer consisting of the layer of the first polyionic material or the third polyionic material and one layer of the second material; and, optionally, (e) repeating steps (c) to (d) for one or more times to build up one or more additional polyelectrolyte bilayers.

This and other aspects of the invention will become apparent from the following description of the presently preferred embodiments. The detailed description is merely illustrative of the invention and does not limit the scope of the invention, which is defined by the appended claims and equivalents thereof. As would be obvious to one skilled in the art, many variations and modifications of the invention may be effected without departing from the spirit and scope of the novel concepts of the disclosure.

DETAILED DESCRIPTION OF PREFERRED EMBODIMENTS

Reference now will be made in detail to the embodiments of the invention, one or more examples of which are set forth below. Each example is provided by way of explanation of the invention, and is not a limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention covers such modifications and variations as come within the scope of the appended claims and their equivalents. Other objects, features and aspects of the present invention are disclosed in or are obvious from the following detailed description. It is to be understood by one of ordinary skill in the art that the present discussion is a description of exemplary embodiments only, and is not intended as limiting the broader aspects of the present invention.

Unless defined otherwise, all technical and scientific terms used herein have the same meaning as commonly understood by one of ordinary skill in the art to which this invention belongs. Generally, the nomenclature used herein and the laboratory procedures are well known and commonly employed in the art. Conventional methods are used for these procedures, such as those provided in the art and various general references. Where a term is provided in the singular, the inventors also contemplate the plural of that term. As employed throughout the disclosure, the following terms, unless otherwise indicated, shall be understood to have the following meanings.

An "article" refers to a medical device or a mold for making a medical device.

A "medical device", as used herein, refers to a device having surfaces that contact tissue, blood, or other bodily fluids of patients in the course of their operation or utility. Exemplary medical devices include: (1) extracorporeal devices for use in surgery such as blood oxygenators, blood pumps, blood sensors, tubing used to carry blood and the like which contact blood which is then returned to the patient; (2) prostheses implanted in a human or animal body such as vascular grafts, stents, pacemaker leads, heart valves, and the like that are implanted in blood vessels or in the heart; (3) devices for temporary intravascular use such as catheters, guide wires, and the like which are placed into blood vessels or the heart for purposes of monitoring or repair; and (4) ophthalmic devices. In a preferred embodiment, medical devices are ophthalmic devices.

An "ophthalmic device", as used herein, refers to a contact lens (hard or soft), an intraocular lens, a corneal onlay, other ophthalmic devices (e.g., stents, implants, or the like) used on or about the eye or ocular vicinity, and cases or containers for storing ophthalmic devices or ophthalmic solutions.

"Biocompatible", as used herein, refers to a material or surface of a material, which may be in intimate contact with tissue, blood, or other bodily fluids of a patient for an extended period of time without significantly damaging the ocular environment and without significant user discomfort.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of protein or lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

A "monomer" means a low molecular weight compound that can be polymerized. Low molecular weight typically means average molecular weights less than 700 Daltons.

A "macromer" refers to medium and high molecular weight compounds or polymers that contain functional groups capable of further polymerization. Medium and high molecular weight typically means average molecular weights greater than 700 Daltons.

"Polymer" means a material formed by polymerizing one or more monomers.

"Surface modification", as used herein, means that an article has been treated in a surface treatment process (or a surface modification process), in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified. Exemplary surface treatment processes include, but are not limited to, a surface treatment by energy (e.g., a plasma, a static electrical charge, irradiation, or other energy source), chemical treatments, the grafting of hydrophilic monomers or macromers onto the surface of an article, and layer-by-layer deposition of polyelectrolytes. A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

"LbL coating", as used herein, refers to a coating obtained by a layer-by-layer ("LbL") alternative, physical deposition of two oppositely charged polymeric materials on an article. In an LbL coating, each layer of a material is non-covalently bond to another layer of a different material. Any suitable deposition techniques can be used in the LbL coating. Exemplary deposition techniques include, without limitation, dipping a substrate into a coating solution and spraying a substrate with a coating solution.

A "charged polymeric material" or a "polyionic material" refers to a charged polymer that has a plurality of charged groups in a solution, or a mixture of charged polymers each of which has a plurality of charged groups in a solution. Exemplary charged polymers includes polyelectrolytes, p- and n-type doped conducting polymers. Charged polymeric materials include both polycationic (having positive charges) and polyanionic (having negative charges) polymeric materials.

The term "bilayer" is employed herein in a broad sense and is intended to encompass, a coating structure formed by applying one layer of a first polyionic material and subsequently one layer of a second polyionic material having charges opposite of the charges of the first polyionic material. It should be understood that the layers of the first and second polyionic materials may be intertwined with each other in the bilayer.

An "innermost layer", as used herein, refers to the first layer of an LbL coating, which is applied onto the surface of a medical device.

A "capping layer", as used herein, refers to the last layer of a coating material which is applied onto the surface of a medical device.

A "polyquat", as used herein, refers to a polymeric quaternary ammonium group-containing compound.

An "averaged value of coefficient of friction" refers to a value, which is obtained by averaging measurements of at least 3 individual medical devices, as described in Example 1. Coefficient of friction (hereinafter CoF) may be one of important parameters that may affect the on-eye movement and thereby the wearer's comfort. High CoF may increase the likelihood of damaging mechanically the ocular epithelia and/or may lead to ocular discomfort.

As used herein, "increased lubricity" in reference to a coated medical device, e.g., a coated contact lens, means that the medical device has a reduced averaged value of CoF relative to an uncoated medical device, wherein both coated and uncoated medical device are made of the same core material.

An "average contact angle" refers to a contact angle (measured by Sessile Drop method), which is obtained by averaging measurements of at least 3 individual medical devices.

As used herein, "increased surface hydrophilicity" or "increased hydrophilicity" in reference to a coated ophthalmic device means that the coated ophthalmic device has a reduced averaged contact angle relative to an uncoated medical device, wherein both coated and uncoated medical device are made of the same core material.

The present invention, in one aspect, provides a method of applying an LbL coating onto a medical device, the method comprising the steps of: (a) contacting said medical device with a first coating solution containing a first polyionic material to non-covalently apply an innermost layer of the first polyionic material onto said medical device, wherein the concentration of the first polyionic material in the first coating solution is sufficiently high enough to increase the hydrophilicity of the LbL coating, and wherein said medical device is not subjected to a surface modification prior to contacting with the first coating solution; (b) contacting said medical device having the innermost layer of the first polyionic material with a second coating solution containing a second polyionic material, to form a first polyelectrolyte bilayer consisting of the innermost layer of the first polyionic material and one layer of the second polyionic material on top of the innermost layer, wherein the second polyionic material has charges opposite of the charges of the first polyionic material; (c) contacting said medical device having the first polyelectroloe bilayer with a third coating solution containing the first polyionic material or a third polyionic material, to form a layer of the first polyionic material or the third polyionic material on top of the first polyelectrolyte bilayer, wherein the third polyionic material has charges opposite of the charges of the second polyionic material; (d) contacting said medical device having the first polyelectrolyte bilayer and one layer of the first polyionic material or the third polyionic material on top of the first polyelectrolyte bilayer with a fourth coating solution containing the second polyionic material or a fourth polyionic material having charges opposite of the charges of the first or third polyionic material, to form a second polyelectrolyte bilayer consisting of the layer of the first polyionic material or the third polyionic material and one layer of the second material; and, optionally, (e) repeating steps (c) to (d) for one or more times to build up one or more additional polyelectrolyte bilayers.

It is discovered unexpectedly that the concentration of a polyionic material in a solution for forming the innermost layer of an LbL coating has a direct, significant impact on the hydrophilicity of the LbL coating on a contact lens. As the concentration of the first polyionic material in the first coating solution increases, the hydrophilicity of a resulting coating on a medical device increases. There is no noticeable correlation between the hydrophilicity of a coating and the concentration of a polyionic material in a coating solution, which is not used in forming the innermost layer of the coating. Based on this unexpected discovery, an improved LbL coating method is developed that can prepare, in a cost-effective fashion, an LbL coating on a medical device with increased hydrophilicity. Such method can also be used to control the hydrophilicity of a coating on a medical device according to one's desire.

The polyionic materials that may be employed in the present invention include polyanionic and polycationic polymers. Examples of suitable polyanionic polymers include, for example, a synthetic polymer, a biopolymer or modified biopolymer comprising carboxy, sulfo, sulfato, phosphono or phosphate groups or a mixture thereof, or a salt thereof, for example, a biomedical acceptable salt and especially an ophthalmically acceptable salt thereof when the article to be coated is an ophthalmic device.

Examples of synthetic polyanionic polymers are: a linear polyacrylic acid (PAA), a branched polyacrylic acid, a polymethacrylic acid (PMA), a polyacrylic acid or polymethacrylic acid copolymer, a maleic or fumaric acid copolymer, a poly(styrenesulfonic acid) (PSS), a polyamido acid, a carboxy-terminated polymer of a diamine and a di- or polycarboxylic acid (e.g., carboxy-terminated Starburst™ PAMAM dendrimers from Aldrich), a poly(2-acrylamido-2-methylpropanesulfonic acid) (poly-(AMPS)), an alkylene polyphosphate, an alkylene polyphosphonate, a carbohydrate polyphosphate or carbohydrate polyphosphonate (e.g., a teichoic acid). Examples of a branched polyacrylic acid include a Carbophil® or Carbopol® type from Goodrich Corp. Examples of a copolymer of acrylic or methacrylic acid include a copolymerization product of an acrylic or methacrylic acid with a vinyl monomer including, for example, acrylamide, N,N-dimethyl acrylamide or N-vinylpyrrolidone. Examples of polyanionic biopolymers or modified biopolymers are: hyaluronic acid, glycosaminoglycanes such as heparin or chondroitin sulfate, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides.

A preferred polyanionic polymer is a linear or branched polyacrylic acid or an acrylic acid copolymer. A more preferred anionic polymer is a linear or branched polyacrylic acid. A branched polyacrylic acid in this context is to be understood as meaning a polyacrylic acid obtainable by polymerizing acrylic acid in the presence of suitable (minor) amounts of a di- or polyvinyl compound.

A suitable polycationic polymer as part of the bilayer is, for example, a synthetic polymer, biopolymer or modified biopolymer comprising primary, secondary or tertiary amino groups or a suitable salt thereof, preferably an ophthalmically acceptable salt thereof, for example a hydrohalogenide such as a hydrochloride thereof, in the backbone or as substituents. Polycationic polymers comprising primary or secondary amino groups or a salt thereof are preferred.

Examples of synthetic polycationic polymers are:
(i) a polyallylamine (PAH) homo- or copolymer, optionally comprising modifier units;
(ii) a polyethyleneimine (PEI);
(iii) a polyvinylamine homo- or copolymer, optionally comprising modifier units;
(iv) a poly(vinylbenzyl-tri-$C_1$–$C_4$-alkylammonium salt), for example a poly(vinylbenzyl-tri-methyl ammoniumchloride);
(v) a polymer of an aliphatic or araliphatic dihalide and an aliphatic N,N,N',N'-tetra-$C_1$–$C_4$-alkyl-alkylenediamine, for example a polymer of (a) propylene-1,3-dichloride or -dibromide or p-xylylene dichloride or dibromide and (b) N,N,N',N'-tetramethyl-1,4-tetramethylene diamine;
(vi) a poly(vinylpyridine) or poly(vinylpyridinium salt) homo- or copolymer;
(vii) a poly(N,N-diallyl-N,N-di-$C_1$–$C_4$-alkyl-ammoniumhalide) comprising units of formula

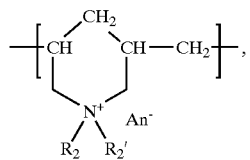

wherein $R_2$ and $R_2'$ are each independently $C_1$–$C_4$-alkyl, in particular methyl, and An⁻ is an anion, for example, a halide anion such as the chloride anion;

(viii) a homo- or copolymer of a quaternized di-$C_1$–$C_4$-alkyl-aminoethyl acrylate or methacrylate, for example a poly(2-hydroxy-3-methacryloylpropyltri-$C_1$–$C_2$-alkylammonium salt) homopolymer such as a poly(2-hydroxy-3-methacryloylpropyltri-methylammonium chloride), or a quaternized poly(2-dimethylaminoethyl methacrylate or a quaternized poly(vinylpyrrolidone-co-2-dimethylaminoethyl methacrylate);
(ix) POLYQUAD® as disclosed in EP-A-456,467; or
(x) a polyaminoamide (PAMAM), for example a linear PAMAM or a PAMAM dendrimer such as an amino-terminated Starbust™ PAMAM dendrimer (Aldrich).

The above mentioned polymers comprise in each case the free amine, a suitable salt thereof, for example a biomedically acceptable salt or in particular an ophthalmically acceptable salt thereof, as well as any quaternized form, if not specified otherwise.

Suitable comonomers optionally incorporated in the polymers according to (i), (iii), (vi) or
(viii) above are, for example, hydrophilic monomers such as acrylamide, methacrylamide, N,N-dimethyl acrylamide, N-vinylpyrrolidone and the like.

Suitable modifier units of the polyallylamine (i) are known, for example from WO 00/31150 and comprise, for example, units of formula

wherein L is $C_2$–$C_6$-alkyl, which is substituted by two or more same, or different substituents selected from the group consisting of hydroxy, $C_2$–$C_5$-alkanoyloxy and $C_2$–$C_5$-alkylamino-carbonyloxy.

Preferred substituents of the alkyl radical L are hydroxy, acetyloxy, propionyloxy, methyl-aminocarbonyloxy or ethylaminocarbonyloxy, especially hydroxy, acetyloxy or propionyloxy and in particular hydroxy.

L is preferably linear $C_3$–$C_6$-alkyl, more preferably linear $C_4$–$C_5$-alkyl, and most preferably n-pentyl, which is in each case substituted as defined above. A particularly preferred radical L is 1,2,3,4,5-pentahydroxy-n-pentyl.

Examples of polycationic biopolymers or modified biopolymers that may be employed in the bilayer of the present invention include: basic peptides, proteins or glucoproteins, for example, a poly-ε-lysine, albumin or collagen, aminoalkylated polysaccharides such as a chitosan or aminodextranes.

Particular polycationic polymers for forming the bilayer of the present invention include a polyallylamine homopolymer; a polyallylamine comprising modifier units of the above formula (II); a polyvinylamine homo- or -copolymer or a polyethyleneimine homopolymer, in particular a polyallylamine or polyethyleneimine homopolymer, or a poly(vinylamine-co-acrylamid)copolymer.

The foregoing lists are intended to be exemplary, but clearly are not exhaustive. A person skilled in the art, given the disclosure and teaching herein, would be able to select a number of other useful polyionic materials.

In order to alter various characteristics of the coating, such as thickness, the molecular weight of the polyionic materials including polyquats can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In accordance with the present invention, the core material of a medical device may be any of a wide variety of polymeric materials. Exemplary core materials include, but are not limited to, hydrogels, silicone-containing hydrogels, polymers and copolymers of styrene and substituted styrenes, ethylene, propylene, acrylates and methacrylates, N-vinyl lactams, acrylamides and methacrylamides, acrylonitrile, acrylic and methacrylic acids.

A preferred group of core materials to be coated are those being conventionally used for the manufacture of biomedical devices, e.g. contact lenses, in particular contact lenses for extended wear, which are not hydrophilic per se. Such materials are known to the skilled artisan and may comprise for example polysiloxanes, perfluoroalkyl polyethers, fluorinated poly(meth)acrylates or equivalent fluorinated polymers derived e.g. from other polymerizable carboxylic acids, polyalkyl(meth)acrylates or equivalent alkylester polymers derived from other polymerizable carboxylic acids, or fluorinated polyolefins, such as fluorinated ethylene or propylene, for example tetrafluoroethylene, preferably in combination with specific dioxols, such as perfluoro-2,2-dimethyl-1,3-dioxol. Examples of suitable bulk materials are e.g. Lotrafilcon A, Neofocon, Pasifocon, Telefocon, Silafocon, Fluorsilfocon, Paflufocon, Silafocon, Elastofilcon, Fluorofocon or Teflon AF materials, such as Teflon AF 1600 or Teflon AF 2400 which are copolymers of about 63 to 73 mol % of perfluoro-2,2-dimethyl-1,3-dioxol and about 37 to 27 mol % of tetrafluoroethylene, or of about 80 to 90 mol % of perfluoro-2,2-dimethyl-1,3-dioxol and about 20 to 10 mol % of tetrafluoroethylene.

Another group of preferred core materials to be coated is amphiphilic-segmented copolymers comprising at least one hydrophobic segment and at least one hydrophilic segment, which are linked through a bond or a bridge member. Examples are silicone hydrogels, for example those disclosed in PCT applications WO 96/31792 to Nicolson et al. and WO 97/49740 to Hirt et al.

A particular preferred group of core materials to be coated comprises organic polymers selected from polyacrylates, polymethacrylates, polyacrylamides, poly(N,N-dimethylacrylamides), polymethacrylamides, polyvinyl acetates, polysiloxanes, perfluoroalkyl polyethers, fluorinated polyacrylates or -methacrylates and amphiphilic segmented copolymers comprising at least one hydrophobic segment, for example a polysiloxane or perfluoroalkyl polyether segment or a mixed polysiloxane/perfluoroalkyl polyether segment, and at least one hydrophilic segment, for example a polyoxazoline, poly(2-hydroxyethylmethacrylate), polyacrylamide, poly(N,N-dimethylacrylamide), polyvinylpyrrolidone polyacrylic or polymethacrylic acid segment or a copolymeric mixture of two or more of the underlying monomers.

The core material to be coated may also be any blood-contacting material conventionally used for the manufacture of renal dialysis membranes, blood storage bags, pacemaker leads or vascular grafts. For example, the material to be modified on its surface may be a polyurethane, polydimethylsiloxane, polytetrafluoroethylene, polyvinylchloride, Dacron™ or Silastic™ type polymer, or a composite made therefrom.

The contacting of the medical device with a solution of, either a polyionic material, a polymeric material or a rinsing solution, may occur by a variety of methods. For example, the medical device may be dipped into a solution. Alternatively, the medical device is sprayed with a solution in a spray or mist form. One coating process embodiment involves solely dip-coating and optionally dip-rinsing steps. Another coating process embodiment involves solely spray-coating and optionally spray-rinsing steps. Of course, a number of alternatives involve various combinations of spray- and dip-coating and optionally spray- and dip-rinsing steps may be designed by a person having ordinary skill in the art.

For example, a solely dip-coating process involves the steps of: (a) immersing a medical device in a first coating solution of a first polyionic material; (b) optionally rinsing the medical device by immersing the medical device in a first rinsing solution; (c) immersing said medical device in a second coating solution of a second polyionic material to form a first polyelectrolyte bilayer of the first and second polyionic materials, wherein the second polyionic material has charges opposite of the charges of the first polyionic material; (d) optionally rinsing said medical device by immersing the medical device in the rinsing solution; (e) immersing said medical device in a third coating solution of the first polyionic material or a third polyionic material having charges opposite of the charges of the second polyionic material to form one layer of the first or third polyionic material on top of the first polyelectrolyte bilayer; (f) optionally rinsing said medical device by immersing the medical device in the rinsing solution; (g) immersing the medical device in a fourth coating solution of the second polyionic material or a fourth polyionic material having charges opposite of the first or third polyionic material to form a second polyelectrolyte bilayer; (h) optionally rinsing the medical device by immersing the medical device in the rinsing solution; and (i) optionally repeating steps (e) to (i) for a number of times. A thicker LbL coating can be produced by repeating steps (e) to (i) preferably for 2 to 40 times.

The immersion time for each of the coating and rinsing steps may vary depending on a number of factors. Preferably, immersion of the core material into the polyionic solution occurs over a period of about 1 to 30 minutes, more preferably about 1 to 20 minutes, and most preferably about 1 to 5 minutes. Rinsing may be accomplished with a plurality of rinsing steps, but a single rinsing step can be quite efficient.

Another embodiment of the coating process involves a series of spray coating techniques. The process generally includes the steps of: (a) spraying on a medical device a first coating solution of a first polyionic material; (b) optionally rinsing the medical device by spraying on the medical device a first rinsing solution; (c) spraying on said medical device a second coating solution of a second polyionic material to form a first polyelectrolyte bilayer of the first and second polyionic materials, wherein the second polyionic material has charges opposite of the charges of the first polyionic material; (d) optionally rinsing said medical device by spraying on the medical device the rinsing solution; (e) spraying on said medical device a third coating solution of the first polyionic material or a third polyionic material having charges opposite of the charges of the second polyionic material to form one layer of the first or third polyionic material on top of the first polyelectrolyte bilayer; (e optionally rinsing said medical device by spraying on the medical device the rinsing solution; (g) spraying on the medical device a fourth coating solution of the second polyionic material or a fourth polyionic material having charges opposite of the first or third polyionic material to form a second polyelectrolyte bilayer; (h) optionally rinsing the medical device by spraying on the medical device the rinsing solution; and (i) optionally repeating steps (e) to (i) for a number of times. A thicker LbL coating can be produced by repeating steps (e) to (i) preferably for 2 to 40 times.

The spray coating application may be accomplished via a process selected from the group consisting of an air-assisted atomization and dispensing process, an ultrasonic-assisted atomization and dispensing process, a piezoelectric assisted atomization and dispensing process, an electromechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. application Ser. No. 60/312199, herein incorporated by reference in its entirety. By using such spraying coating processes, an asymmetrical coating can be applied to a medical device. For example, the back surface of a contact lens can be coated with a hydrophilic and/or lubricous coating material and the front surface of the contact lens can be coated with an antimicrobial material. It is also possible to produce a coating on a contact lens, the coating having a functional pattern so as to provide simultaneously multiple benefits to a wearer.

A preferred number of bilayers in a biocompatible LbL coating of the invention are about 5 to about 20 bilayers. While more than 20 bilayers are possible, it has been found that delamination may occur in some LbL coatings having an excessive number of bilayers.

A biocompatible LbL coating of the invention can be formed from at least three different polyionic materials.

A biocompatible LbL coating of the invention can comprise at least one layer of a lubricious coating material which is selected from the group consisting of PAMAM dendrimers, PAAm-co-PAA, PVP-co-PAA, glycosaminoglycanes, fucoidan, poly-aspartic acid, polyglutamic acid, carboxymethyl cellulose, carboxymethyl dextrans, alginates, pectins, gellan, carboxyalkyl chitins, carboxymethyl chitosans, sulfated polysaccharides, glucoproteins, and aminoalkylated polysaccharides.

A biocompatible LbL coating of the invention can comprise at least one layer of a polyquat.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors.

It may be typical to formulate a relatively dilute aqueous solution of charged polymeric material. For example, a charged polymeric material concentration can be between about 0.0001% to about 0.25% by weight, between about 0.005% to about 0.10% by weight, or between about 0.01% to about 0.05% by weight.

However, where a coating solution containing a first polyionic material is used to form an innermost layer of a biocompatible LbL coating of the invention on the surface of a medical device, it is desirable that the concentration of the first charged polymeric material in the solution is sufficiently high enough to increase the hydrophilicity of the LbL coating. Preferably, the concentration of the charged polymeric material in a solution for forming the innermost layer of an LbL coating is at least three folder higher than the concentration of a coating material in a coating solution for forming subsequent layers of the LbL coating. More preferably, the concentration of the charged polymeric material in a solution for forming the innermost layer of an LbL coating is at least ten folder higher than the concentration of a coating material in a coating solution for forming subsequent layers of the LbL coating.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

Polycationic solutions can also be formed in a manner as described above. For example, in one embodiment, poly (allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

An LbL coating of the present invention may find particular use in extended-wear contact lenses. The LbL coating of the invention may have a minimal adverse effects on the desirable bulk properties of the lens, such as oxygen permeability, ion permeability, and optical properties.

A medical device of the invention can be made by applying a biocompatible LbL coating to a preformed medical device according to an above-described method of the invention.

In addition to polyionic and non-charged polymeric materials, a coating solution for forming the bilayer or part of it, can also contain additives. As used herein, an additive can generally include any chemical or material. For example, active agents, such as antimicrobials and/or antibacterials can be added to a solution forming the bilayer, particularly when used in biomedical applications. Some antimicrobial polyionic materials include polyquaternary ammonium compounds, such as those described in U.S. Pat. No. 3,931,319 to Green et al. (e.g. POLYQUAD®).

Moreover, other examples of materials that can be added to a coating solution are polyionic materials useful for ophthalmic lenses, such as materials having radiation absorbing properties. Such materials can include, for example, visibility-tinting agents, iris color modifying dyes, and ultraviolet (UV) light tinting dyes.

Still another example of a material that can be added to a coating solution is a polyionic material that inhibits or induces cell growth. Cell growth inhibitors can be useful in devices that are exposed to human tissue for an extended time with an ultimate intention to remove (e.g. catheters or Intra Ocular Lenses (IOL's), where cell overgrowth is undesirable), while cell growth-inducing polyionic materials can be useful in permanent implant devices (e.g. artificial cornea).

When additives are applied to a coating solution, such additives, preferably, have a charge. By having a positive or negative charge, the additive can be substituted for the polyionic material in solution at the same molar ratio. For example, polyquaternary ammonium compounds typically have a positive charge. As such, these compounds can be substituted into a solution of the present invention for the polycationic component such that the additive is applied to the core material of an article in a manner similar to how a polycationic would be applied.

It should be understood, however, that non-charged additives can also be applied to the core material of an article by entrapment.

Moreover, the core material to be coated may also be an inorganic or metallic base material without suitable reactive groups, e.g. ceramic, quartz, or metals, such as silicon or gold, or other polymeric or non-polymeric substrates. e.g., for implantable biomedical applications, ceramics are very useful. In addition, e.g. for biosensor purposes, hydrophilically coated base materials are expected to reduce nonspecific binding effects if the structure of the coating is well controlled. Biosensors may require a specific carbohydrate coating on gold, quartz, or other non-polymeric substrates.

The form of the material to be coated may vary within wide limits. Examples are particles, granules, capsules, fibers, tubes, films or membranes, preferably moldings of all kinds such as ophthalmic moldings, for example intraocular lenses, artificial cornea or in particular contact lenses.

The previous disclosure will enable one having ordinary skill in the art to practice the invention. In order to better enable the reader to understand specific embodiments and the advantages thereof, reference to the following examples is suggested.

EXAMPLE 1

Measurements of CoF of Coated Contact Lenses

COF may be one of parameters that measure the easiness of the on-eye movement of a contact lens. High CoF may increase the likelihood of damaging mechanically the ocular epithelia. CoF of a contact lens can be measured by a sled-on-block type of friction tester as follow. Under a certain load (e.g., about 2.0 grams), a contact lens is slid back and forth, at a prescribed speed, against a biologically relevant substrate and both the normal force (N) and the tangential force ($F_T$) are measured. The CoF of the contact lens is calculated based on the equation of $\mu=F_T/N$.

A preferred friction tester comprises: a stationary lens holder assembly, a biologically relevant substrate, a horizontally movable platform, and a plurality of force measuring means.

The stationary lens holder assembly preferably comprises an "A-shaped" holder bracket and a lens holder having a lens-supporting surface. The lens-supporting surface of the lens holder has a convex curvature capable of accommodating the back (concave) surface of a contact lens. The lens holder is preferably held by a means in the center of the "A-shaped" holder bracket. The head end of the "A-shaped" stationary sample holder bracket is connected to a first force measuring means (e.g., a load cell from Transducer Techniques) by, for example, a Kevlar® fiber. The two foot-ends of the "A-shaped" holder bracket are connected to nylon string attached with two ½" steel extension springs. The first force measuring means and the steel extension springs are mounted to the frame of the tester.

The horizontally movable platform can be, for example, a table platform (x-table) which moves uniaxially at various speeds and accelerations. The x-table preferably has a dimension of 163 mm long and 19.1 mm wide and can provide a test area having about 140 mm long and about 14.7 mm wide. An example of the x-table is a Model 41 Linear Positioner, which is powered by a ZETA Drive Compumotor (Parker Hannifin Corporation), which operates unidirectional at maximum velocities of 1800 mm/min and accelerations of 9000 mm/s².

The biologically relevant substrate can be any material and preferably is a powder-free surgical glove with Biogel® Coating" from Regent®. Preferably, the finger of the glove is cut into a single rectangular strip, and stretched and attached to the x-table by a physical means, for example, jumbo paper clips. Before testing, the substrate attached onto the x-table is lubricated with two drops of a desired lubricant, for example, ultra pure water or Softwear® saline (CIBA vision). Any air between the substrate and the x-table should be removed. The desired lubricant should be applied evenly on the substrate. The substrate should be even and consistent throughout.

Preferably, there are three force-measuring means, a first, a second and a third force-measuring means. Any suitable known force-measuring means can be used. An example is a 100-gram load cells from Transducer Techniques. The first force-measuring means is attached to the sample holder to measure tangential forces (friction forces, $F_T$) in two opposite directions. The second and third force-measuring means reside under the x-table to measure normal force (N) in the downward direction. The other load cell Values outputted by the normal load cells are converted to grams by a Versatile Amplifier/Conditioner (Transducer Techniques).

Measurements of CoF are performed on the preferred friction tester as follows. A contact lens is placed on a lens holder with the back surface of the contact lens against the lens-supporting surface of the lens hold. The lens holder with the contact lens is assembled with the "A-shaped" holder bracket and then placed in contact with a desired lubricated substrate. This substrate is mounted to a horizontally movable table platform that is capable of moving uniaxially at various speeds and accelerations. About 3 grams of weight is loaded onto the lens holder. This load may represent the force pressed on a contact lens by a blink of eyelids. The three force-measuring means (3 Load cells from Transducer Techniques) measure simultaneously the normal (N) and frictional ($F_T$) forces that are produced from the interaction between the contact lens and the substrate lubricated with a desired lubricant. Multiple data points are taken during a measurement of lubricity/lubricating drag/ coefficient of friction of a contact lens. At each data point, CoF $\mu$, is calculated as follows:

$$\mu=F_T/N$$

in which $F_T$ represent actual data reading at each point obtained by the first force measuring means after correcting for the preloading provided by the springs (tangential load cell) during sliding of the substrate against the contact lens and preferably has a unit of gram; N is the sum of $N_1$ and N2; N1 represents actual data reading at each point obtained by the second force-measuring means after correcting for any preloading by the test assembly (normal load cell#1) during sliding of substrate against the contact lens and preferably has a unit of gram; and $N_2$ represents actual data reading at each point obtained by the third force-measuring means after correcting for any preloading by the test assembly (normal load cell#2) during sliding of substrate against the contact lens and has preferably a unit of gram. The average ($\mu_{Ave}$) of all $\mu$'s at every data point will be used to represent the value of CoF, of a contact lens.

More preferably, the friction tester further comprises a computer system that controls the tester, collects readings of the normal and tangential forces simultaneously as the biologically-relevant substrate interacts with contact lens, calculates CoF, and records and charts the forces ($F_T$ and N) and CoF ($\mu$) at each data point during testing.

EXAMPLE 2

Measurements of Contact Angles of Coated Contact Lenses

Average contact angles (Sessile Drop) of contact lenses are measured using a VCA 2500 XE contact angle measurement device from AST, Inc., located in Boston, Mass. This equipment is capable of measuring advancing or receding contact angles or sessile (static) contact angles. The measurements are preferably performed on fully hydrated materials.

The contact angle is a general measure of the surface hydrophilicity of a contact lens. In particular, a low contact angle corresponds to more hydrophilic surface. The averaged contact angle of a contact lens, which is made of lotrafilcon A and without any coating (LbL or plasma), is about 112 degree.

EXAMPLE 3

Polyacrylic acid (PAA) solutions: Two solution of polyacrylic acid having a molecular weight of about 90,000, from Polyscience, Inc., is prepared by dissolving a suitable amount of the material in water to have a desired concentration of PAA. The PAA concentration is calculated based on the repeating unit in PAA. Once dissolved, the pH of the polyanionic PAA solution is adjusted by adding 1N hydrochloric acid until the pH is about 2.5.

Poly(allylamine hydrochloride) (PAH) solution: A solution of poly(allylamine hydrochloride) (PAH) having a molecular weight of about 70,000, from Aldrich, is prepared by dissolving a suitable amount of the material in water to form a 0.001M PAH solution. The concentration is calculated based on the molecular weight of repeating unit in PAH. Thereafter, the pH of the polycationic PAH solution is measured and recorded. The pH is around 4.5.

Coating A: A coating having 5 bilayers of PAA/PAH are formed on a soft contact lens made of a fluorosiloxane hydrogel material, lotrafilcon A (CIBA Vision). The contact lens is dipped with the help of a Zeiss coater in a PAA solution (0.0001M, pH 2.5) for 30 minutes to form the innermost layer of the coating on the lens and then rinsed with water by dipping with the help of a Zeiss coater in water for 1 minute. The lens with the innermost layer of PAA is then dipped with the help of a Zeiss coater in a PAH solution (0.0001M, pH 2.5) for 5 minutes, rinsed with water by dipping with the help of a Zeiss coater in water, dipped with the help of a Zeiss coater in the PAA solution (0.0001M, pH 2.5) for 5 minutes, and then rinsed by dipping with the help of a Zeiss coater in water. The steps of dipping with the help of a Zeiss coater in the PAH solution for 5 minutes followed by dipping with the help of a Zeiss coater in the PAA solution for 5 minutes are repeated for 4 times to build up 4.5 bilayers (i.e., PAA/PAH/PAA/PAH/PAA/PAH/PAA/PAH/PAA on the lens. The lens with the 4.5 bilayers is dipped with the help of a Zeiss coater in the PAH solution for 5 minutes and then released into a phosphate buffered saline (PBS) (ca. pH 7.2). Each of the coated lenses is placed and sealed in one glass vial filled with PBS buffer and autoclaved. After autoclave, vials containing a coated lens are not opened until lens characterization.

Coating B: A coating having 4.5 bilayers of PAA/PAH are formed on a soft contact lens made of a fluorosiloxane hydrogel material, lotrafilcon A (CIBA Vision). The contact lens is dipped manually in a first PAA solution (0.001M, pH 2.5) for 30 minutes to form the innermost layer of the coating on the lens and then rinsed with water by dipping manually in water for 1 minute. The lens with the innermost layer of PAA is then dipped manually in a PAH solution (0.0001M, pH 2.5) for 5 minutes, rinsed with water by dipping manually in water, dipped manually in a second PAA solution (0.0001M, pH 2.5) for 5 minutes, and then rinsed by dipping manually in water. The steps of dipping in the PAH solution for 5 minutes followed by dipping in the second PAA solution for 5 minutes are repeated for 4 times to build up 4.5 bilayers (i.e., PAA/PAH/PAA/PAH/PAA/PAH/PAA/PAH/PAA on the lens. Each of the coated lenses is placed and sealed in one glass vial filled with a phosphate buffered saline (PBS) (ca. pH 7.2) and autoclaved. After autoclave, vials containing a coated lens are not opened until lens characterization.

It is discovered unexpectedly that the concentration of $1^{st}$ dip solution (i.e., the first PAA solution) appears to have a direct impact on the hydrophilicity of the lens coating. The LbL coated lenses with the $1^{st}$ dipping in the 0.001M PAA solution have an average contact angle of from about 42 degrees. The LbL coated lenses with the $1^{st}$ dipping in the 0.0001M PAA have an average contact angle of from about 87 degrees.

EXAMPLE 4

PAA and PAH solutions: PAA and PAH solutions are prepared as described in Example 3.

Coating C: A coating having 4.5 bilayers of PAA/PAH are formed on a soft contact lens made of a fluorosiloxane hydrogel material, lotrafilcon A (CIBA Vision). The contact lens is coated as follows: (a) manually dipping in a PAA solution (0.0001M, pH 2.5) for 30 minutes to form the innermost layer of the coating on the lens; (b) without water rinsing, manually dipping in a PAH solution (0.0001M, pH 2.5) for 5 minutes; (c) without water rinsing, manually dipping in the PAA solution (0.0001M, pH 2.5) for 5 minutes; (d) repeating steps (b) to (c) for 3 times to build up 4.5 bilayers (i.e., PAA/PAH/PAA/PAH/PAA/PAH/PAA/PAH/PAA) on the lens. Each of the coated lenses is placed and sealed in one glass vial filled with a phosphate buffered saline (PBS) (ca. pH 7.2) and autoclaved. After autoclave, vials containing a coated lens are not opened until lens characterization.

Coating D: A coating having 4.5 bilayers of PAA/PAH are formed on a soft contact lens made of a fluorosiloxane hydrogel material, lotrafilcon A (CIBA Vision). The contact lens is coated as follows: (a) manually dipping in a first PAA solution (0.001M, pH 2.5) for 30 minutes to form the innermost layer of the coating on the lens; (b) without water rinsing, manually dipping in a PAH solution (0.0001M, pH 2.5) for 5 minutes; (c) without water rinsing, manually dipping in a second PAA solution (0.0001M, pH 2.5) for 5 minutes; repeating steps (b) to (c) to (d) for 3 times to build up 4.5 bilayers (i.e., PAA/PAH/PAA/PAH/PAA/PAH/PAA/PAH/PAA) on the lens. Each of the coated lenses is placed and sealed in one glass vial filled with a phosphate buffered saline (PBS) (ca. pH 7.2) and autoclaved. After autoclave, vials containing a coated lens are not opened until lens characterization.

Coating E: A coating having 4.5 bilayers of PAA/PAH are formed on a soft contact lens made of a fluorosiloxane hydrogel material, lotrafilcon A (CIBA Vision). The contact lens is coated as follows: (a) manually dipping in a first PAA solution (0.01M, pH 2.5) for 30 minutes to form the innermost layer of the coating on the lens; (b) without water rinsing, manually dipping in a PAH solution (0.0001M, pH 2.5) for 5 minutes; (c) without water rinsing, manually dipping in a second PAA solution (0.0001M, pH 2.5) for 5 minutes; (d) repeating steps (b) to (c) to (d) for 3 times to build up 4.5 bilayers (i.e., PAA/PAH/PAA/PAH/PAA/PAH/PAA/PAH/PAA') on the lens. Each of the coated lenses is placed and sealed in one glass vial filled with a phosphate buffered saline (PBS) (ca. pH 7.2) and autoclaved. After autoclave, vials containing a coated lens are not opened until lens characterization.

The hydrophilicity of an LbL coating formed on a contact lens depends on the concentration of a polyionic material in a first coating solution to form the innermost layer of the polyionic material (Table 1). The concentration of the polyionic material in the first coating solution increases from 0.0001M (PAA) to 0.001M (PAA) and to 0.010M (PAA), averaged contact angles decrease from 74±11 degrees to 54±8 degrees and to 37±8 degrees.

TABLE 1

| | Concentration[a] | Contact angle[b] (n = 10) |
|---|---|---|
| Coating C | 0.1 mM PAA, pH 2.5 | 74 ± 11 |
| Coating D | 1 mM PAA, pH 2.5 | 54 ± 8 |
| Coating E | 10 mM PAA, pH 2.5 | 37 ± 8 |

[a]The concentration of PAA in the first coating solution.
[b]Contact angles averaged over measurements of 10 contact lenses.

All results shown in the above examples demonstrate that the hydrophilicity of an LbL coating on a contact lens can be enhanced by using a relatively high concentration of a polyionic material in a coating for forming the innermost layer of the LbL coating. A LbL-coated contact lens having a relatively high hydrophilicity characterized by an averaged contact angle of less than 50 degrees can be achieved by adjusting the concentration of a polyionic material in a coating solution for forming the innermost layer of the LbL coating, while maintaining the desired bulk properties such as oxygen permeability and ion permeability of lens material. Such lenses are useful as extended-wear contact lenses.

Although various embodiments of the invention have been described using specific terms, devices, and methods, such description is for illustrative purposes only. The words used are words of description rather than of limitation. It is to be understood that changes and variations may be made by those skilled in the art without departing from the spirit or scope of the present invention, which is set forth in the following claims. In addition, it should be understood that aspects of the various embodiments may be interchanged either in whole or in part. Therefore, the spirit and scope of the appended claims should not be limited to the description of the preferred versions contained therein.

What is claimed is:

1. A method for applying a biocompatible layer-by-layer coating onto a medical device, comprising the steps of:

(a) contacting said medical device with a first coating solution containing a first polyionic material to non-covalently apply an innermost layer of the first polyionic material onto said medical device, and wherein prior to contacting with the first coating solution said medical device is not subjected to a surface modification;

(b) contacting said medical device having the innermost layer of the first polyionic material with a second coating solution containing a second polyionic material, to form a first polyelectrolyte bilayer consisting of the innermost layer of the first polyionic material and one layer of the second polyionic material on top of the innermost layer, wherein the second polyionic material has charges opposite of the charges of the first polyionic material;

(c) contacting said medical device having the first polyelectrolyte bilayer with a third coating solution containing the first polyionic material or a third polyionic material, to form a layer of the first polyionic material or the third polyionic material on top of the first polyelectrolyte poilayer, wherein the third polyionic material has charges opposite of the charges of the second polyionic material;

(d) contacting said medical device having the first polyelectrolyte bilayer and one layer of the first polyionic material or the third polyionic material on top of the first polyelectrolyte bilayer with a fourth coating solution containing the second polyionic material or a fourth polyionic material having charges opposite of the charges of the first or third polyionic material, to form a second pelyelectrolyte bilayer consisting of the layer of the first polyionic material or the third polyionic material and one layer of the second material; and, optionally, (e) repeating steps (c) and (d) for a number of times to build up additional polyelectrolyte bilayers until formation of the layer by layer coating on the medical device, wherein the concentration of the first polyionic material in said first coating solution is selected to be at least ten times higher than the concentration of any polyionic material in any coating solution other than the first coating solution so as to impart to the layer-by-layer coating a relatively high hydrophilicity characterized by an averaged contact angle of less than about 54 degrees.

2. A method of claim 1, comprising at least a rinsing step between steps (a) and (b), between steps (b) and (c), between steps (c) and (d), or between steps (d) and (c), wherein the rinsing step is carried out by contacting said medical device with a rinsing solution.

3. A method of claim 1, comprising no rinsing step between steps (a) and (b), between steps (b) and (c), between steps (c) and (d), or between steps (d) and (c).

4. A method of claim 1, wherein at least one of said contacting occurs by spraying a solution onto the medical device.

5. A method of claim 1, wherein at least one of said contacting occurs by dipping said medical device into a coating solution.

6. A method of claim 1, wherein said method comprises repeating steps (a) through (d) between 3 to 20 times.

7. A method of claim 1, wherein the concentration of the first polyionic material in said first coating solution is from 10 to 25 folds of the concentration of the first, second, third, or fourth polyionic material in the second, third or fourth coating solution.

8. A method of claim 1, wherein the third coating solution contains the first polyionic material.

9. A method of claim 1, wherein the third coating solution contains the third polyionic material.

10. A method of claim 1, wherein the fourth coating solution contains the second polyionic material.

11. A method of claim 1, wherein the fourth coating solution contains the fourth polyionic material.

12. A method of claim 1, wherein at least three different polyionic materials are used in forming the biocompatible LbL coating on said medical device.

13. A method of claim 1, wherein the biocompatible LbL coating comprises at least one layer of a lubricious coating material or a polyquat, wherein the lubricious coating material is selected from the group consisting of polyaminoamide dendrimers, polyacrylamide-polyacrylic acid copolymers (PAAm-co-PAA), polyvinylpyrrolidone/polyacrylic acid copolymers (PVP-co-PAA), glycosaminoglycanes, fucoidan, poly-aspartic acid, poly-glutamic acid, carboxymethyl cellulose, carboxymethyl dextrans, alginates, pectins, gellan, carboxyalkyl chitins, carboxymethyl chitosans, sulfated polysaccharides, glucoproteins, and aminoalkylated polysaccharides.

* * * * *